(12) United States Patent
Dalton et al.

(10) Patent No.: US 6,231,746 B1
(45) Date of Patent: May 15, 2001

(54) DIRECT ELECTROCHEMISTRY OF ENZYMES

(75) Inventors: Howard Dalton, Long Itchington; Hugh Allen Oliver Hill, Iffley; Jurate Kazlauskaite, Kenilworth, all of (GB); Patricia Callahan Wilkins, Albuquerque, NM (US)

(73) Assignee: BG plc, Berkshire (GB)

( * ) Notice: Subject to any disclaimer, the term of this patent is extended or adjusted under 35 U.S.C. 154(b) by 0 days.

(21) Appl. No.: 09/180,279

(22) PCT Filed: May 8, 1997

(86) PCT No.: PCT/GB97/01251

§ 371 Date: Mar. 18, 1999

§ 102(e) Date: Mar. 18, 1999

(87) PCT Pub. No.: WO97/43632

PCT Pub. Date: Nov. 20, 1997

(30) Foreign Application Priority Data

May 10, 1996 (GB) .................................................. 9609809
May 10, 1996 (GB) .................................................. 9609810

(51) Int. Cl.[7] .............................. C25B 3/00; C12N 13/00; C12N 11/00
(52) U.S. Cl. ........................ 205/413; 435/173.1; 435/174
(58) Field of Search ................................. 435/173.1, 174, 435/817; 205/413; 427/435

(56) References Cited

U.S. PATENT DOCUMENTS 4,374,013 * 2/1983 Enfors .............................. 204/195 B

OTHER PUBLICATIONS

Wong et al., "Direct Electrochemistry of Putidaredoxin at a Modified Gold Electrode", J. of Electroanal. Chem., vol. 389, pp. 201–203, 1995 no month available.*

Gou et al., "Direct Un–Mediated Electrochemistry of the Enzyme p–Cresolmethylhydroxylase", J. Electroanal. Chem., vol. 266, pp. 379–396, 1989 no month available.*

Lotzbeyer et al., "Direct Electron Transfer Between the Covalently Immobilized Enzyme Microperoxidase MP–11 and a Cystamine–Modified Gold Electrode", J. of Electroanal. Chem., vol. 377, pp. 291–294, 1994 no month available.*

* cited by examiner

Primary Examiner—Edna Wong
(74) Attorney, Agent, or Firm—Oblon, Spivak, McClelland, Maier & Neustadt, P.C.

(57) ABSTRACT

A method of electrochemistry is conducted by conducting the direct electrochemistry of a monooxygenase enzyme in the absence of mediators. A method of electrochemistry is conducted by conducting the direct electrochemistry of an hydroxylase enzyme in the absence of mediators.

21 Claims, 5 Drawing Sheets

DIRECT ELECTROCHEMISTRY OF ENZYMES

This is a national stage application of PCT/GB97/01251 filed May 8, 1997.

BACKGROUND OF THE INVENTION

1. Field of the Invention

The present invention relates to the electrochemistry of enzymes, in particular the electrochemistry of hydroxylase or monooxygenase enzymes.

2. Description of the Background

Hydroxylases are known as catalysts for the oxidation of various substrates. For example, methane monooxygenase is an efficient catalyst for the oxidation of methane by molecular oxygen to give methanol as the sole product.

Studies of the structure and mechanisms of electrochemistry of hydroxylases have been reported in the literature.

There are two forms of the enzyme methane monooxygenase, soluble (sMMO) and particulate (pMMO). The soluble enzyme from *Methylococcus capsulatus* (Bath) consists of an hydroxylase (Mw 250.5 kDa), a reductase (Mw 38.5 kDa) and a regulatory component, protein B (Mw 15.9 kDa) all of which are required for activity. The hydroxylase is made up of two protomers in an a2b2g2 arrangement and the X-ray crystal structure of this component has been solved. The sMMO from *Methylosinus trichosporium* OB3b has a very similar composition and has also been well characterised. The active site in sMMO is a di-iron centre, bridged by an hydroxo group (in the resting enzyme), which resides in the a subunit of the hydroxylase. Reducing equivalents from NADH are transferred to active site through $F_2S_2$ and FAD centres in the reductase. Protein B contains no metal ions or cofactors and the details of its regulatory role are unclear. In the resting enzyme the irons are in the fully oxidised Fe(III)Fe(III) state. There are two other oxidation states readily available to the di-iron cluster, namely, the mixed valent Fe(III)Fe(II) and the fully reduced Fe(II)Fe(II) states. It is the Fe(II)Fe(II) form of the hydroxylase which reacts with and activates $O_2$ during enzyme turnover.

The redox potentials of the di-iron centres in *M. capsulatus* (Bath) and *M. trichosporium* OB3b have been measured in three independent studies. The (electrode potential) values for the Fe(III)Fe(III)/Fe(III)Fe(II) and Fe(III)Fe(II)/Fe(II)Fe(II) couples have been the subject of some debate. The redox properties of the hydroxylase component of soluble methane monooxygenase from the two different organisms have been extensively investigated. Previous studies used redox indicator titrations and spectroscopic methods for the determination of the concentrations of reduced species. Indirect titration of the hydroxylase di-iron centres with redox active mediators were employed in these studies. The concentrations of the mixed valent and fully reduced hydroxylase species were determined by EPR (electron-proton resonance) or EPR and Moessbauer spectroscopy at very low temperatures (4.2–18° K).

In the field of protein electrochemistry, thiol- or disulfide-containing organic molecules have been found to be particularly good modifiers because they chemisorb through a strong gold-surfer bond thereby giving a stable layer of surface coverage on the electrode. Relevant amino acids may also be chemisorbed in this fashion and thus promote protein electrochemistry at the electrode surface. The use of cysteine containing peptides which also contain functional amino acids (e.g. arginine, lysine, histidine), as promoters for protein electrochemistry has been investigated.

However, contrary to the field of protein electrochemistry, it is not a trivial task to carry out direct electrochemical measurements without the aid of mediators, on redox enzymes. A major difficulty is that often the redox centres are buried deep within the protein, far from the surface, so that the distance electrons must traverse to an electrode can be large enough to reduce the rate of electron transfer to a negligibly small value. Also as most redox enzymes are much larger and structurally less rigid than non-redox proteins, they are more liable to deformation and lose of activity on electrode surfaces.

The electrochemistry of hydroxylases in the presence of a mediator is complicated by the possibility of interaction between the hydroxylase and the mediator, while the mediator may disturb the determination of species concentrations at temperatures different from those at which the redox reactions are carried out.

SUMMARY OF THE INVENTION

It is an object of the present invention to avoid the aforesaid disadvantages.

According to one aspect of the present invention a method for the transfer of electrons between an electrode and an enzyme in an electrochemical process comprises causing the enzyme to adhere to the electrode.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
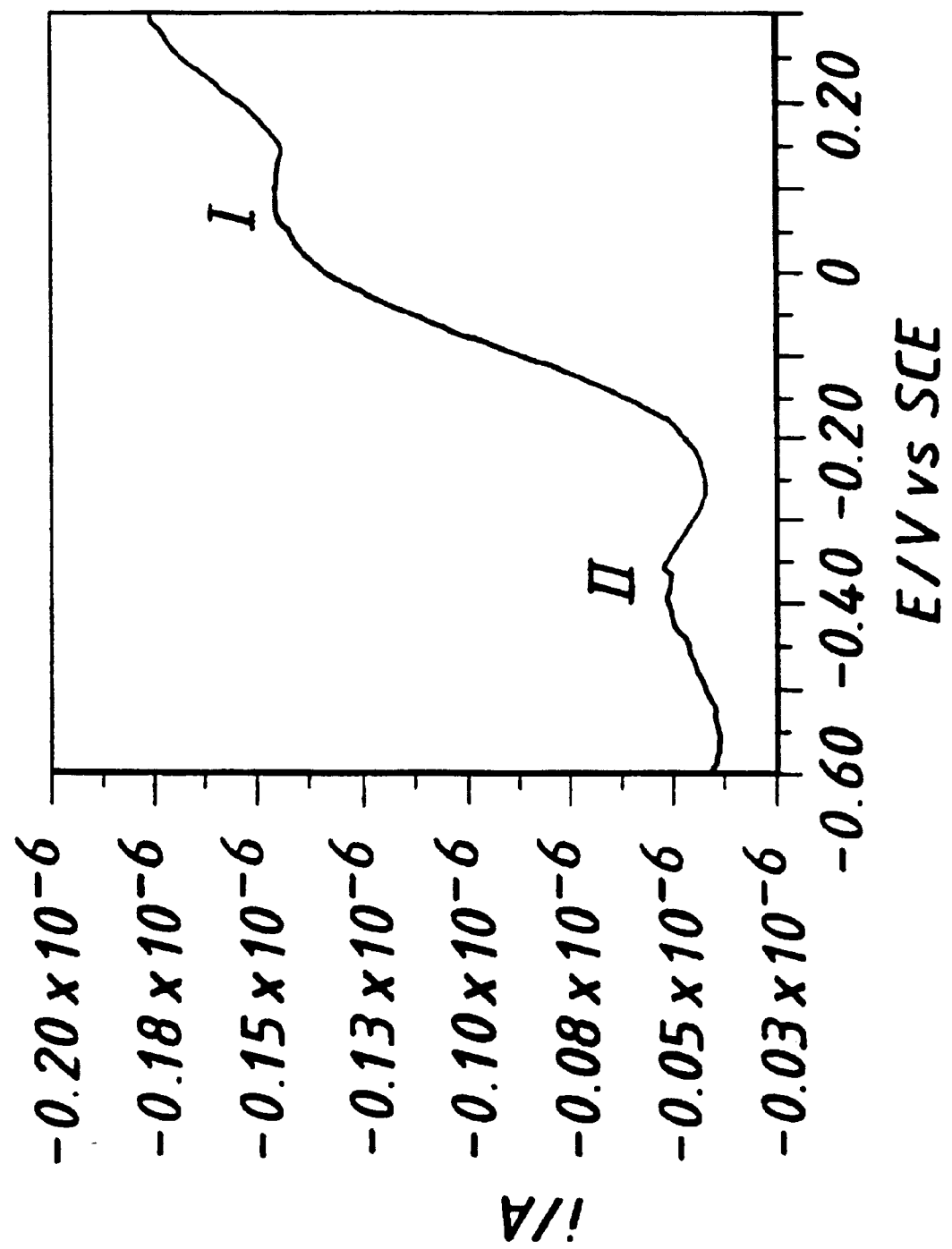
FIG. 1 shows a differential voltammogram of 23.6 mM hydroxylase solutions at a polypeptide modified gold electrode in 40 mM MOPS, pH 7.0.

Preferably the transfer is direct.

According to another aspect of the present invention a method for the electrochemistry of an enzyme comprises direct electrochemistry carried out in the absence of mediators.

In one embodiment of the invention, the enzyme is a monooxygenase.

In another embodiment of the invention, the enzyme is a P450 (an enzyme known in the art) or modified P450.

In a further embodiment of the invention, the enzyme is methane monooxygenase.

In a still further embodiment of the invention, the enzyme is an hydroxylase.

The hydroxylase may be a soluble methyl monooxygenase.

The enzyme may contain a di-iron centred active site or alternatively the enzyme may contain a porphyrin-containing active site.

Preferably the electrochemistry is carried out using a modified gold electrode.

According to a further aspect of the invention, the process for modifying an electrode to render the electrode suitable for use in the electrochemistry of an enzyme in the absence of mediators, comprises treating the electrode with a peptide.

Preferably the enzyme is a monooxygenase.

Suitably the enzyme has a di-iron or porphyrin-containing active site.

Conveniently the peptide comprises a hexapeptide.

Preferably the hexapeptide contains cys and lys residues.

Suitably the hexapeptide is lys-cys-thr-cys-cys-ala.

Conveniently the treatment involves voltammetric cycling the electrode in a solution of the hexapeptide while avoiding reductive cleaning of the electrode.

According to a still further aspect of the present invention, a process for the oxidation of a substrate by molecular oxygen in the presence of an enzyme, comprises direct electrochemistry carried out in the absence of mediators.

In one embodiment of the invention, the enzyme is a monooxygenase.

In another embodiment of the invention, the enzyme has a di-iron or porphyrin-containing active site.

The substrate may be methane which is oxidised to methanol, or the substrate may be camphor and is oxidised to 5-exo-hydroxycamphor or the substrate comprises polycyclic aromatic hydrocarbons which are oxidised to 5-exo-hydroxycamphor.

The hydroxylase is preferably derived from cytochrome P450cam.

Suitably, cysteine is removed from the reaction medium.

We have found that an electrode modified with peptides provides a more congenial surface to attract an enzyme.

We believe that, for electron transfer between the hydroxylase component of $M.$ capsulatus (Bath) sMMO and an electrode to occur, a positively charged surface is preferred: The e-amino group of the lys residue in the preferred hexapeptide presumably fulfils this role. Electrochemical modification of the electrode with this particular peptide provides a stable monolayer and more uniform surface coverage compared to an electrode modified by chemisorption (ie. simply dipping the electrode in the peptide solution).

The electrode may be a modified gold electrode, for example a gold electrode modified by treatment with the hexapeptide lys-cys-thr-cys-cys-ala. The treatment may be carried out by cycling the electrode in a solution of the hexapeptide, while avoiding reductive cleaning of the electrode.

The effect of both protein B and protein B' upon the electrochemistry of hydrolase solutions is important. EPR spectroscopy of the mixed valent state has shown that protein B binding to the hydroxylase alters the environment around the di-iron site. In each of these previous studies it was also observed to cause a shift in the di-iron potentials.

Formation of an hydroxylase-protein B complex is known to alter the properties of the di-iron site, affect product distribution and increase the rates of formation of some of the intermediates in the SMMO catalytic cycle. All of these effects may be due to the ability of protein B to induce a conformational change in the hydroxylase when it binds to it, which is transmitted to the active site. We have found that the redox potentials of the hydroxylase are affected by the presence of protein B as was observed in previous studies. It has been suggested that the negative shift in the redox potentials caused by protein B binding to the hydroxylase is due to a change in the first coordination sphere of the iron(s) or a change in the protonation state of the hydroxo bridge. Other effects such as change in solvent accessibility or the structure of the active site environment, caused by conformational changes upon protein B binding, could also account for the changes in the potentials. We estimate Kd for the Fe(II)Fe(II) complex to be $2.06\pm0.23$ M and $7.01\pm0.45$ M for Fe(II)Fe(III) complex. Therefore, the decrease in the redox potentials may simply be a reflection of the decreased affinity between the hydroxylase and protein B components, depending on the oxidation state of the former.

In the $M.$ capsulatus (Bath) enzyme system, two forms of the regulatory protein B are routinely purified. These are the full length protein B and a twelve amino acid truncate, protein B'. Binding studies using surface plasmon resonance (SPR) show that protein B' also forms a complex with the fully oxidised hydroxylase, which is only three times less stable than the corresponding protein B complex. Our investigations suggest that protein B' binds at the same site as protein B, but that the former is unable to cause the same conformational change in the hydroxylase which is transmitted to the di-iron centre and which alters the redox potentials and other properties of the active site. The formation of the truncated protein B' may therefore have some regulatory role in the organism. Under certain conditions protein B is cleaved to form protein B' and the conformational change (and attendant active site property alterations) in the hydroxylase can occur. In this way the cell may be able to conserve scarce resources when under stress. We have found that direct electrochemistry, without the intervention of mediators, is possible with a non-electron transfer protein which is as large as the hydroxylase component of soluble methane monooxygenase.

As mentioned previously the process may be, for example, the oxidation of methane to methanol or the oxidation of camphor to 5-exo-hydroxycamphor, in particular the oxidation of camphor to 5-exo-hydroxycamphor using a hydroxylase derived from cytochrome P450cam. In the latter process, we have found it advisable to remove cysteine from the reaction medium.

Porphyrin centred hydroxylases which are native to the bacterium Pseudomonas putida (grown on camphor) is an ideal system to study the regulation of electron transfer between two redox centres in separate protein molecules.

Cytochrome P450cam catalyses the monooxygenation of D-(+)-camphor to give 5-exo-hydroxy camphor for which an external source of two reducing equivalents is required. These electrons are transferred from NADH to the haem iron of P450cam throughout the combined action of the FAD-flavoprotein putidaredoxin reductase and the iron-sulphur protein putidaredoxin. Dramatic changes observed in the haem optical spectrum upon camphor binding have been shown in Mossbauer and EPR studies to be due to a shift in the spin-state of the ferrihaem iron, from low-spin in the absence of substrate to high-spin in the substrate-bound protein. In addition, it has been noted that this spin-state change upon camphor binding is accompanied by a redox potential change from $-540$ mV to $-414$ mV (vs. SCE). This shift in the haem reduction potential is key feature of the P450cam catalytic cycle, allowing the first electron transfer from putidaredoxin to occur and thus initiating catalytic turnover.

We have found that the cathodic peak current exhibits a linear dependence on the square root of the scan rate ($\sqrt{v}$) for camphor-bound P450cam, indicating that the overall process is diffusion controlled.

However, deviation from linearity has been observed for the camphor-free enzyme. This may be caused either by adsorption to the electrode surface, or by the fact that the heterogeneous electron transfer process is no longer diffusion controlled. The first of these is unlikely because the global structures of camphor-bound and camphor-free P450cam are very similar, and thus both forms are expected to have similar affinities for the electrode surface. This therefore implies that the rate of heterogeneous electron transfer to the camphor-free form is lower than that to the camphor-bound form. This could be due to the relatively high reorganisation required to produce the five-coordinate, high-spin ferrous form from the six-coordinate, low-spin camphor-free enzyme, which entails the loss of the haem-bound water ligand. This requirement is similar to that for the reduction of myoglobin which has been shown to have a high reorganisation energy compared to the reduction of cytochrome, which has six-coordinate haem irons in both ferric and ferrous forms.

With the camphor-bound P450cam, both the ferric and ferrous forms of the enzyme have five-coordinate, high spin haem iron, and the reorganisation barrier to both homogeneous and heterogeneous electron transfer should be low.

The electrochemical response of P450cam at a bare, negatively charged epg (edge-plane pyrolytic graphite) electrode strongly suggests that, despite the overall negative charge of the protein at pH 7.4 (pI (isoelectric point)=4.55) a specific pattern of positively charged surface amino acid residues favours an interaction between the enzyme and the electrode surface in such a way that heterogeneous electron transfer can take place. Computer modelling and mutagenesis studies indicate that the basic residues Arg-72, Arg-112, Arg-364 and Lys-344 on the surface of P450cam interact with acidic residues on the surface of putidaredoxin in the complex between these two proteins. From the high resolution crystal structure of P450cam, these surface residues are on the proximal side of the haem and in the region of the enzyme where the haem is closest (ca.10A) to the surface. Since the electron transfer rate constant generally decrease with donor acceptor separation, it is reasonable to assume that this region on the surface of P450cam will form both the binding site for putidaredoxin and the region of interaction with the electrode. Thus it appears that these positively charged residues are also involved in the interaction between P450cam and the bare epg electrode.

Thus an edge-plane graphite electrode can successful replace the chain of physiological electron transfer proteins in the first electron transfer to cytochrome P450cam, the direct electrochemistry being substrate dependent.

FIG. 1 shows a Differential voltammogram of 23.6 mM hydroxylase solutions at a lys-cys-thr-cys-cys-ala modified gold electrode in 40 mM MOPS, pH 7.0 (the background current has been subtracted).

Figure 2B:
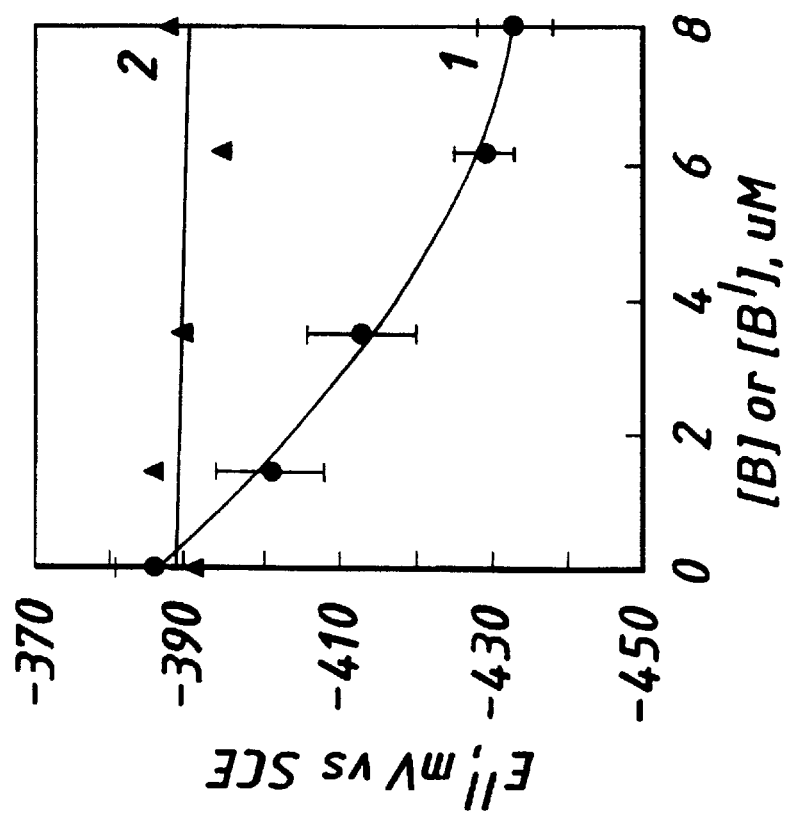
FIGS. 2A and 2B show the effect of increasing concentrations of protein B (1) or B' (2) on the potentials of the first (a) and second (b) electron transfer.
Figure 2A:
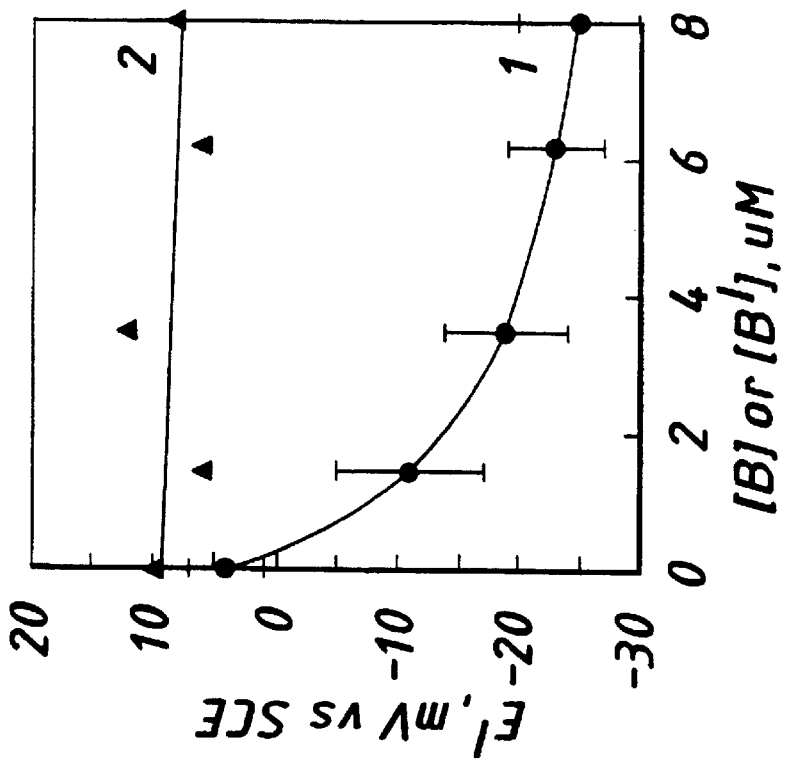

FIGS. 2A and 2B show the effect of increasing concentrations of protein B (1) or B' (2) on the potentials of the first (a) and second (b) electron transfer. [Hydroxylase]=21 mM, 40 mM MOPS, pH 7.0. The electrode was measured prior to each measurement.

Figure 3B:
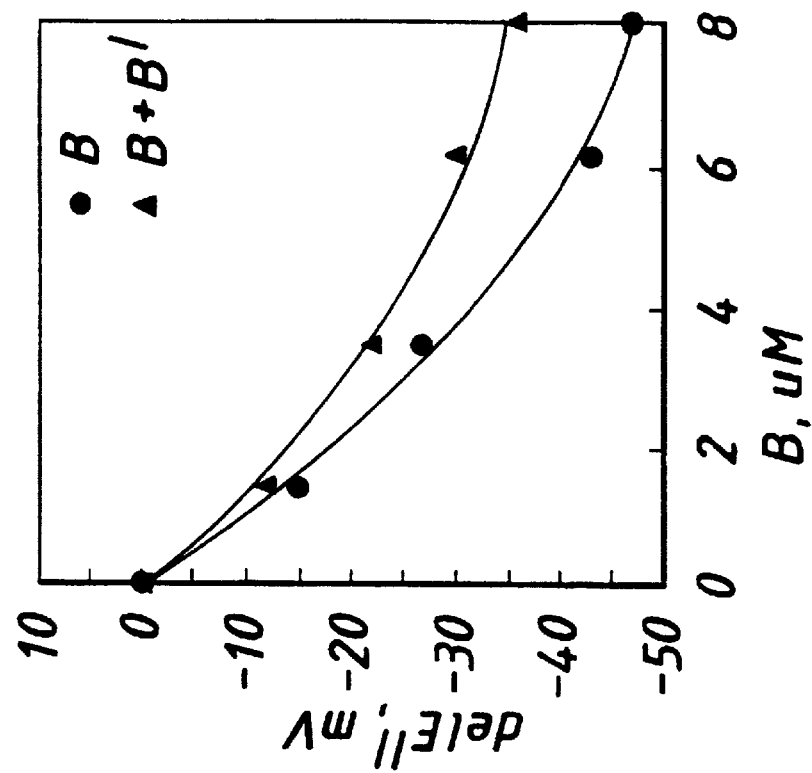
FIGS. 3A and 3B show the effect of increasing concentrations of protein B on the potentials of the first (a) and second (b) electron transfer in the presence of protein B'.
Figure 3A:
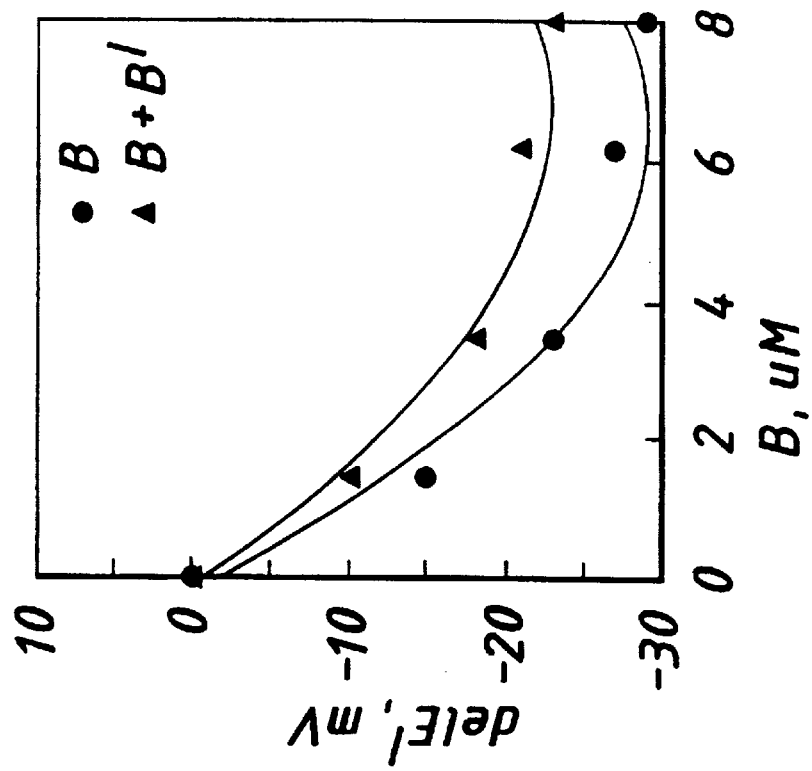

FIGS. 3A and 3B show the effect of increasing concentrations of protein B on the potentials of the first (a) and second (b) electron transfer in the presence of protein B'. [Hydroxylase=21 mM, [B']=4 mM, 40 mM, pH 7.0.

Figure 4:
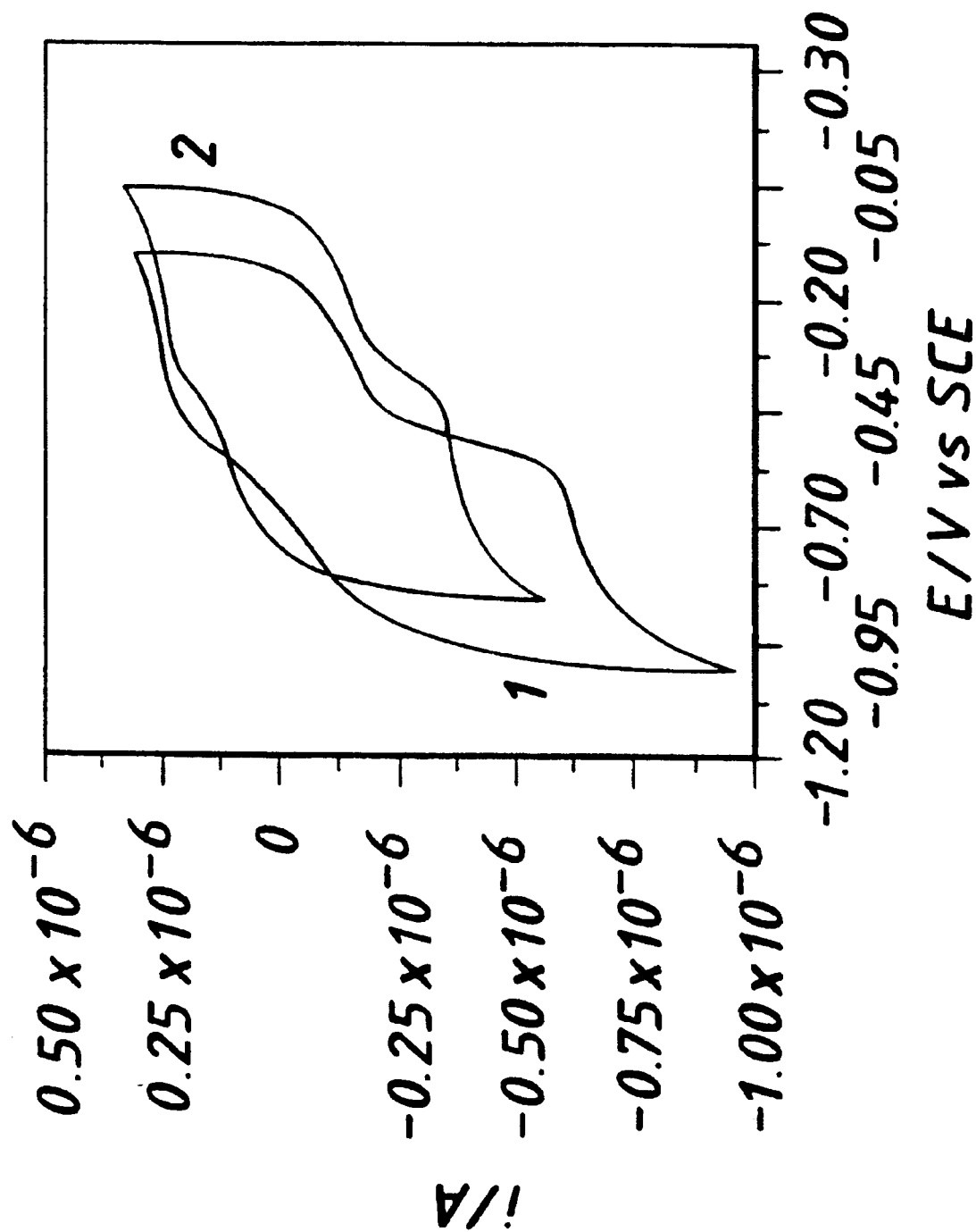
FIG. 4 shows the cyclic volt monograms of cytochrome P450cam.

FIG. 4 shows the cyclic voltammograms of cytochrome P450cam.

Figure 5:
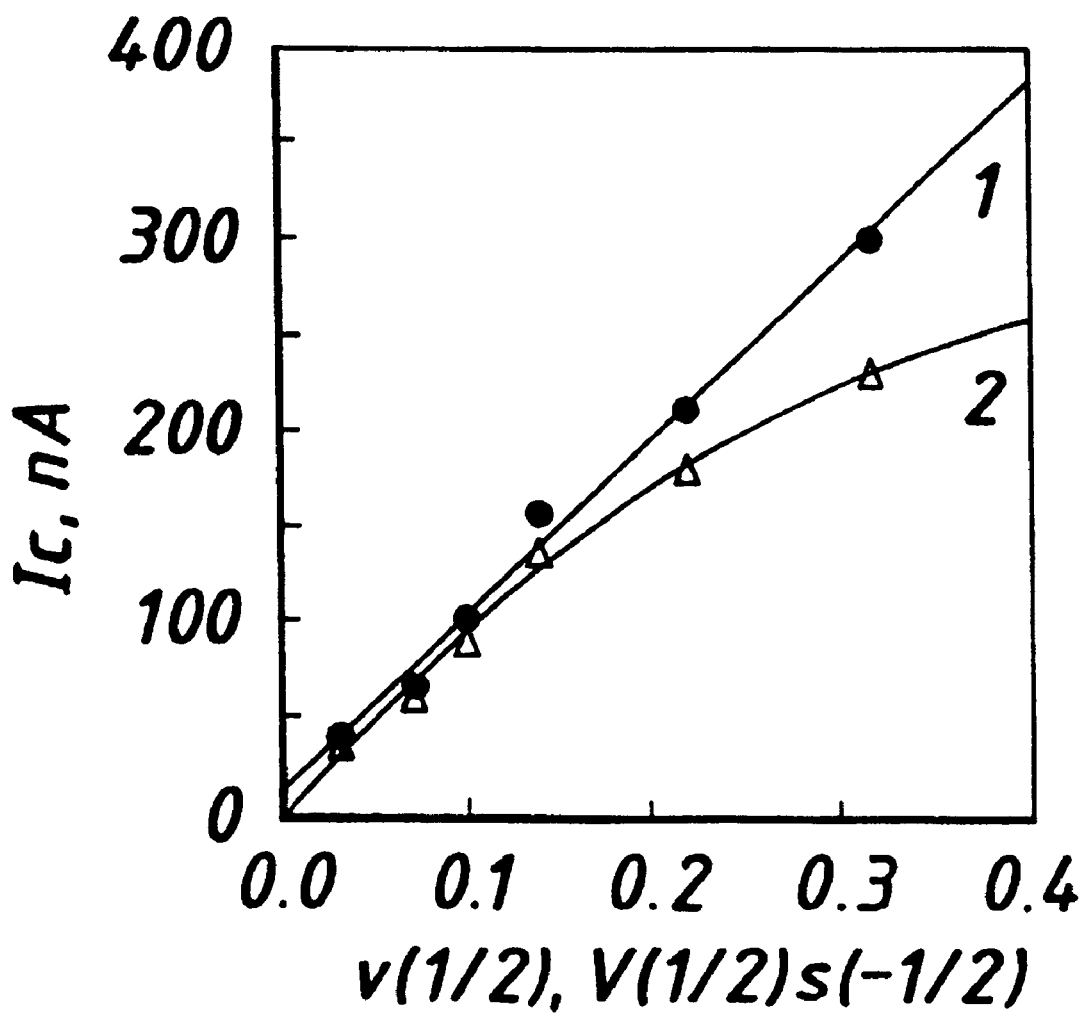
FIG. 5 shows the dependence of the cathodic peak current on the potential scan rate for camphor-bound and camphor-free cytochrome P450cam.

FIG. 5 shows the dependence of the cathodic peak current on the potential scan rate for camphor-bound and camphor-free cytochrome P450cam.

Having now generally described this invention, a further understanding can be obtained by reference to certain specific examples which are provided herein for purposes of illustration only and are not intended to be limiting unless otherwise specified.

EXAMPLES (I) Growth of the Enzyme

Growth of *Methylococcus capsulatus* (Bath) organism was carried out as described in Pilkington, S. J. & Dalton, H. (1990) "Soluble Methane Monooxygenase from *Methylococcus capsulatus* (Bath)". Methods in Enzymol. 188, 181–190.

In the purification of the hydroxylase and protein B components, the following modifications of the published procedures were employed: After the initial ion exchange step, the hydroxylase was applied to a SUPERDEX 200 gel infiltration column. Final purification was by elution of pure hydroxylase from a Mono Q ion exchange column using a 0–30% gradient of 1M NaCl. Protein B was purified in a similar manner except that the gel filtration medium was SUPERDEX 75.

(ii) Modification of the Electrodes

Gold electrodes were modified by cycling the electrode at reducing potentials in a 5 mM solution of hexapeptide lys-cys-thr-cys-cys-ala. When performing the reductive cycle, care was taken not to exceed a limit of −0.85 V, because the reduction of protons to hydrogen has the effect of reductively cleaning gold surfaces. Ten cycles were found to give adequate modification. The hexapeptide used to modify the gold electrode, was purchased from Sigma Chemical Company, Poole, Dorset.

(iii) Redox Potential Measurements

Differential pulse voltammetry (DPV) was the method chosen to measure the redox potentials of the hydroxylase di-iron centres.

DPV experiments with the sMMO hydroxylase produced two waves at 4±10 (wave I in FIG. 1) and −386±144 mV (wave II in FIG. 1) during the cathodic scan. The peaks are attributed to the first and second electrons being transferred to the hydroxylase di-iron centre.

Differential pulse voltammetry (DPV) was performed at a conventional stationary polycrystalline gold (4 mm diameter) disc electrode arranged in a small volume (300–400 ml), three-electrode, two compartment glass cell. A saturated calomel electrode (SCE) (Radiometer K-401) served as the reference electrode. All potentials herein are in reference to a SCE. All experiments were performed in 40 mM MOPS buffer at pH 7.0 and 23° C.

(iv) Effects of Proteins B and B'

In addition, the effects of proteins B and B' on the redox reactions were determined.

Further experiments were carried out with the addition of the regulatory protein B to the solution used for differential pulse voltammetry to determine if there was any effect of its presence on the hydroxylase electrochemistry. In these experiments, protein B was added to the hydroxylase in a maximum ratio of 2:1 (B:hydroxylase). Higher B:hydroxylase ratios resulted in a decrease in both current peaks to negligibly small values, probably due to electrode fouling. The electrode was modified before measurement with each different protein B concentration to ensure maximum uniform, fresh coverage. As shown in FIGS. 2A and 2B increasing the concentration of protein B resulted in a shift of both the first and second wave peak potentials toward more negative values. However, each potential was affected differently. The overall shift in the first potential was 29 mV, but was 47 mV for the second. This is due to the different binding constants for protein B when the hydroxylase di-iron centre is in the mixed valent or fully reduced states.

Dissociation constants. Kd=2.06±0.23 M and 7.01±0.45 M were determined for protein B binding to the Fe(III)Fe(II) and Fe(II)Fe(II) forms of the hydroxylase, respectively, according to the method described in Klotz, I. M. & Hunston, D. L. (1970) "Properties of Graphical Representations of Multiple Classes of Binding Sites", Biochem. 10, 3065–3069. As can be seen from FIGS. 2A and 2B, the addition of pure protein B', the truncated form of protein B had no effect on the electrochemistry of the sMMO hydroxylase. However, in a B+B' mixture, the effect of protein B on the potential shift becomes less pronounced and a slight increase in Kd for both reduced states of the protein was observed. In the presence of protein B', Kd=3.49±0.17 M for the mixed valent and Kd=8.50±0.20 M for the fully reduced state were estimated for the hydroxylase-protein B complexes. This finding indicates that a B+B' mixture, reduction of the hydroxylase somehow becomes limited. The reduction potentials and binding constants of the hydroxylase-protein B complexes under the various conditions investigated are summarised in Table 1.

method with the modified gold electrode. The reduction of the fully oxidised Fe(III)Fe(III) form to the mixed valent Fe(II)Fe(III) state occurs at 4±10 while the potential for the formation of fully reduced Fe(II)Fe(II) species was determined to be −368±10 mV (E"). These values differ from those previously reported which, as stated above, differ among themselves (Table 2.). At present there is no clear explanation for these differences but the preparation, purity and activity of the proteins used in each study, as well as some morphological differences between the *M. trichosporium* OB3b and *M. capsulatus* (Bath) hyroxylases may be relevant. However, the hydroxylase components from the two organisms have essentially identical spectroscopic characteristics and very similar homology as well as similar substrate specificities. Therefore, other possible sources of the discrepancies among the electrochemical results must be considered. It has already been suggested that one possible source of error is dependence on the absolute quantitation of the EPA spectra of only one of the three redox states of SMMO hydroxylase as a means to determine the extent of overall reduction. Another source could be in the method of measurement itself. The earlier multi-component reaction mixtures were composed of a set of redox dyes (for calibrating the potential axis), dithionite or reduced methylviologen as reductants and ferriciniumcarboxylic acid as oxidant. The interactions occurring between the protein and these components might affect the redox potentials and a specific case of redox indicator interaction with hydroxylase has been reported. In addition, there may be some temperature dependence associated with these potentials.

The EPR and Mossbauer measurements were carried out at 4.2–18 K.

TABLE 1

Reduction potentials (mV vs SCE) and binding constants for the sMMO hydroxylase from *Methylococcus capsulatus* (Bath). Experimental conditions are described in Materials and Methods.

| Components | E' (mV) | E" (mV) | Kd, mMFe (II) Fe (II) | Kd, mMFe (II) Fe (II) .B |
|---|---|---|---|---|
| hydroxylase 23 mM | +4 ± 10 | −386 ± 14 | 2.06 ± 0.23 | 7.01 ± 0.45 |
| hydroxylase 17 mM + protein B 8 mM + | −25 ± 14 | −433 ± 8 | 2.06 ± 0.23 | 7.01 ± 0.45 |
| hydroxylase 17 mM + protein B 8 mM + protein B' 4 mM | −13 ± 17 | −430 ± 9 | 3.49 ± 0.17 | 8.50 ± 0.20 |

Previous studies of the redox properties of the hydroxylase component of sMMO gave quite a wide range of redox potentials for the individual electron transfer steps. Two formal redox potentials for *M. capsulatus* (Bath were determined using redox indicator titration and EPR spectroscopy. The extent of reduction was monitored solely by spin quantitation of the characteristic EPR spectrum of the mixed valent state. Woodland et al. reported values of E'=−106 mV and E"=−269 mV and those of Liu were E'=−196 mV and E"=−379 mV and in more recent measurements E'=−144 mV and E"=−344 mV.

In the studies of *M. trichosporium* OB3b sMMO, Mossbauer spectroscopy was used in parallel with EPR spectroscopy to determine the concentrations of reduced species. The *M. trichosporium* OB3b sMMO titration resulted in formal potentials of E'=−168 mV and E"=−233 mV.

These data on the redox potentials of the SMMO hydroxylases are summarised in Table 2. In this study the redox potentials values have been determined for the individual electron transfer steps using a direct electrochemical

TABLE 2

Summary of the reduction potentials reported for the hydroxylase component of sMMO.

| Protein source | E' mV (vs NHE) | E", mV (vs NHE) | Reference |
|---|---|---|---|
| *M. capsulatus* (Bath) | +106 (+350) | −269 (−25) | 6 |
| *M. capsulatus* (Bath) | −144 (+100) | −344 (−100) | 1 |
| *M. capsulatus* (Bath) | −196 (+48) | −379 (−135) | 7 |
| *M. trichosporium* OB3b | −168 (+76) | −223 (+21) | 8 |
| *M. capsulatus* (Bath) | +4 (+248) | −386 (−142) | this work |

Table I illustrates the relationship between the redox potentials and protein B binding to the hydroxylase when the di-iron centre is in different oxidation states. In spite of the differences in the *M. capsulatus* (Bath) and *M. trichosporium* OB3b reduction potentials (Table 2), the dissociation constants for the two Fe(III)Fe(II). B complexes are similar, ie. Kd=2.06 mM for the former and Kd=1.7 mM for the latter. However, the dissociation constants for the Fe(II)Fe(II) B complexes vary considerably, ie. Kd=7.01 mM for *M. capsulatus* (Bath) and Kd=500 mM for OB3b.

Interesting effects are observed when protein B' is present in the hydroxylase solution to be electrochemically reduced. Protein B' alone does not have any effect on the redox behaviour of the hydroxylase. However, the binding of protein B becomes less strong in the presence of protein B' and results in a slightly higher observed Kd of 3.49±0.17 M for Fe(II)Fe(III) form and of 8.5±0.20 M for Fe(II)Fe(II) complex. This indicates that protein B' also binds to the hydroxylase, but does not form as strong a complex, which is in agreement with the EPR results.

(v) Electrochemistry

Unmediated, direct electrochemistry of the sMMO hydroxylase di-iron centres was undertaken using modified gold electrodes.

(vi) Use of cytochrome P450cam

FIG. 4 shows the cyclic voltammograms on an edge-plane graphite electrode of (1) 15 M cytochrome pH 7.4 and (2) 18 M cytochrome P450cam in 40 mM potassium phosphate buffer, pH 7.4 containing 1 mM D-(+)-camphor. The camphor-bound form of the enzyme shows a similarly shaped response (FIG. 4) at −390 10 mV. These potentials, and the shift in potential on camphor binding of 136 mV to a more positive value, are in reasonable agreement with earlier potentiometrically determined values of −540 mV and −414 mV respectively.

FIG. 5 shows the dependence of the cathodic peak current on the potential scan rate for camphor-bound and camphor-free cytochrome P450cam. Conditions are as in FIG. 1, except that the temperature was 18° C. The cathodic peak current exhibits a linear dependence on the square root of the scan rate ($\sqrt{v}$) for camphor-bound P450cam, indicating that the overall process is diffusion controlled.

(vii) Electrochemical Conversion of camphor to 5-exo-hydroxy camphor

Having achieved the electrochemistry of cytochrome P450cam, the enzyme was used in the conversion of camphor to 5-exohydroxy camphor. The enzyme was constrained at the electrode surface by use of an Eastman membrane, AQ40. The potential was varied from ±0.2 V to −0.8 V slowly scanning at 50 mV/s; dioxygen was bled into the solution and periodically the system was analysed for 5-exo-hydroxy camphor. It was found the formation of 5-exo-hydroxy camphor increased to 100% after 2 hours.

While the present specification includes theoretical statements concerning the mechanisms by which certain processes referred to herein are thought to proceed, it is not intended that the present invention is to be limited by such statements.

What is claimed is:

1. A method of electrochemistry, comprising:
   conducting the direct electrochemisty of a monooxygenase enzyme in the absence of mediators.

2. The method as claimed in claim 1, wherein the enzyme contains a di-iron centered active site.

3. The method as claimed in claim 1, wherein the enzyme contains a porphyrin-containing active site.

4. The method as claimed in claim 1, wherein the enzyme is a P450 or a modified P450.

5. The method as claimed in claim 1, wherein the electrochemistry involves the direct transfer of enzymes.

6. The method as claimed in claim 1, wherein the electrochemistry is conducted with a modified gold electrode.

7. A method of electrochemistry comprising:
   conducting the direct electrochemistry of an hydroxylase enzyme selected from the group consisting of methyl monooxygenase, an hydroxylase enzyme containing a di-iron centered active site, an hydroxylase enzyme containing a porphyrin-containing active site and P450 or a modified P450 in the absence of mediators.

8. The method as claimed in claim 7, wherein the electrochemistry involves the direct transfer of enzymes.

9. The method as claimed in claim 7, wherein the electrochemistry is conducted with a modified gold electrode.

10. A process of oxidation, comprising:
    conducting the direct electrochemistry of a substrate by molecular oxygen in the presence of a monooxygenase enzyme in the absence of mediators.

11. The process as claimed in claim 10, wherein the hydroxylase component of said monooxygenase is derived from cytochrome P450 cam.

12. The process as claimed in claim 11, wherein cysteine is removed from the reaction medium.

13. A process of oxidation, comprising:
    conducting the direct electrochemistry of methanol to methanol by molecular oxygen in the presence of an enzyme in the absence of mediators.

14. The process as claimed in claim 13, wherein said enzyme is a hydroxylase derived from cytochrome P450 cam.

15. The process as claimed in claim 14, wherein cysteine is removed from the reaction medium.

16. A process of oxidation, comprising:
    conducting the direct electrochemistry of camphor to 5-exo-hydroxycamphor by molecular oxygen in the presence of an enzyme in the absence of mediators.

17. The process as claimed in claim 16, wherein said enzyme is a hydroxylase derived from cytochrome P450 cam.

18. The process as claimed in claim 17, wherein cysteine is removed from the reaction medium.

19. A process of oxidation, comprising:
    conducting the direct electrochemistry of polycyclic aromatic hydrocarbons to 5-exo-hydroxycamphor by molecular oxygen in the presence of an enzyme in the absence of mediators.

20. The process as claimed in claim 19, wherein said enzyme is a hydroxylase derived form cytochrome P450 cam.

21. The process as claimed in claim 20, wherein cysteine is removed from the reaction medium.

* * * * *

UNITED STATES PATENT AND TRADEMARK OFFICE
CERTIFICATE OF CORRECTION

PATENT NO. : 6,231,746 B1
DATED : May 15, 2001
INVENTOR(S) : Howard Dalton et al.

It is certified that error appears in the above-identified patent and that said Letters Patent is hereby corrected as shown below:

Column 1,
Line 46, "The (electrode potential)" should read -- The Eo' (electrode potential) --;

Column 2,
Line 12, "lose of" should read -- loss of --;
Line 46, "volt monograms" should read -- voltammograms --.

Column 5,
Line 55, "can successful" should read -- successfully --;
Line 59, "Differential" should read -- differential --.

Column 7,
Line 51,"(Bath" should read -- (Bath) --;
Line 63,"SMMO" should read -- sMMO --;
Line 66,"potentials values" should read -- potential values --.

Column 8,
Line 20, "SMMO" should read -- sMMO --;

Column 9,
Line 2, "(II) B complexes" should read -- (II).B complexes --.

Column 10,
Line 30, "of methanol to" should read -- of methane to --.

Signed and Sealed this

Twenty-ninth Day of January, 2002

*Attest:*

*Attesting Officer*

JAMES E. ROGAN
*Director of the United States Patent and Trademark Office*